United States Patent [19]

Mason

[11] 3,987,498

[45] Oct. 26, 1976

[54] ELECTRIC ELBOW
[75] Inventor: Carl Peter Mason, Oceanside, N.Y.
[73] Assignees: Sidney Samole; Myron M. Samole
[22] Filed: July 1, 1974
[21] Appl. No.: 484,948

Related U.S. Application Data

[63] Continuation-in-part of Ser. No. 171,658, Aug. 12, 1971, abandoned.

[52] U.S. Cl. .......................................... 3/1.1; 3/12.3
[51] Int. Cl.$^2$ ......................... A61F 1/06; A61F 1/00
[58] Field of Search ............... 3/1.1, 1, 1.2, 12–12.8

[56] References Cited

UNITED STATES PATENTS

| | | | |
|---|---|---|---|
| 2,445,711 | 7/1948 | Fitch | 3/12.1 |
| 2,822,551 | 2/1958 | Alderson | 3/12.2 |
| 3,173,151 | 3/1965 | Glabiszewski | 3/12.7 |

FOREIGN PATENTS OR APPLICATIONS

| | | | |
|---|---|---|---|
| 1,902,700 | 8/1970 | Germany | 3/1 |

OTHER PUBLICATIONS

*Bulletin of Prosthetic Research*, BPR 10–12 Fall 1969, pp. 326–335 relied upon.

*Bulletin of Prosthetic Research*, BPR 10–10 Fall 1968, pp. 261–264 relied upon.

*Bulletin of Prosthetic Research*, BPR 10–11 Spring 1969, pp. 286–288 relied upon.

*Reinforced Plastics and Composites World*, May/June 1968, "The Expanding World of Reinforcements", pp. 9–13.

Primary Examiner—Ronald L. Frinks
Attorney, Agent, or Firm—Stephen Wyden

[57] ABSTRACT

An electrical rotator designed as a prosthetic joint, useable as a remote manipulator and particularly suitable as an electric elbow providing very light weight, high strength, and low cost, incorporating among other features a planetary roller wave generator, totally enclosed motor, integral molding, and a planetary race to achieve desirable performance characteristics.

21 Claims, 12 Drawing Figures

ELECTRIC ELBOW

This is a continuation in part of patent application Ser. No. 171,658 filed Aug. 12, 1971, now abandoned and is entitled to the priorities of the filed parent application.

The purpose of designing an electric elbow is to produce a unit that will perform, weigh, and appear comparable to a normal elbow at a marketable price. Such units can also be used as remote controlled rotators-manipulators. I have accomplished this in my invention through the novel use of a novel two piece molded plastic housing with an integrally molded spline, a balanced force system wherein as the output load is increased (output torque) the harmonic drive teeth change part of this to equal radial loads on the planetary rollers, the sun in the center supports these forces and balances one against the other (especially valuable in the improved wave generator body), and a totally enclosed coaxially supported power train. The balanced forces contribute to minimizing wear, minimal parts and maximal power output while the coaxial mounting of the power train minimizes power losses and helps the unit align itself.

Weight reductions have been accomplished through the use of light weight materials and a minimum number of parts, thereby also contributing to the low cost of the unit.

In particular, the elbow consists of the following parts: A baseplate, in one version, for attaching the elbow to the conventional existing humeral section turntable; two housing elements, an active and a passive side, both formable in the same mold but with a hole in one element for passing through the output tang attaching it to a forearm section, and a hole in the other housing element for pivotally mounting the forearm and possibly counterbalancing the terminal device perhaps with a spring loaded mechanism or other methods of adding weights to the device in such a way that the effective mass of the device is distributed in a manner that can be moved smoothly and with a minimum of effort, counterbalances are discussed in the catalog of Springs of the Associated Spring Corporation under the heading of Constant Tension Springs; where the baseplate is not used the housing elements can be molded with an integral quick disconnect for easy attachment to a mating part in the humeral section; a flexspline with integrally molded output tang for attaching to the (driven) forearm unit; a motor driven planetary roller wave generator harmonic drive assembly supplying the power to the flexspline; and a limit assembly designed to electrically limit the travel of the flexspline.

The limit assembly is designed to stop the motor rapidly when it reaches its desired limit of travel and prevent it from going further by shunting the motor in the forward direction, making it act as a generator, and stopping additional power for movement in that direction from reaching the motor while allowing power to be fed to the motor for movement in the reverse direction in order to drive the elbow off its limit, or end, position. The entire system acts as a generator when it is provided a shunt by a controller or limiting device; in this mode of operation it instantaneously stops, because the high efficiency action of the bell wound motor or torque servo motor acts as a D.C. generator and the motor cannot generate power into a shunt. The value of the bell wound servo motors is their light weight and high effeciency as generators per unit power. They are available from Micro Mo Electronics Inc., Cleveland, Ohio. Once stopped, the static friction value exceeds the dynamic friction value and the elbow is maintained in the stopped position even though dynamically the system efficiency may be greater than 50% at maximum load. The motor driven planetary roller wave generator assembly generates balanced normal forces (and torque) because the planetary rollers are restrained (or are self restraining) and operate in intimate contact with the sun, which is the motor shaft in this case. In addition, using two planets in the assembly allows maximum reduction ratios, few parts and less weight.

The motor is either of the skew wound bell shaped servo type or the permanent magnet D.C. torque type which provide lightest weight, highest obtainable efficiencies and, when shunted, act as high efficiency generators. The motor is coaxially mounted in the flexspline, is supported by the flexspline, and supports the two planetary roller bearings.

The noise produced by this elbow is minimized by totally enclosing the motor within the flexspline of the harmonic drive which in turn is enclosed by the two housings and, if used, the baseplate; also by the use of smooth roller surfaces for the planets and the sun and by a totally balanced symmetrical drive system which reduces the bearing support requirements.

The use of integral molding techniques and electronic circuitry, where possible, have permitted minimization of size and weight factors while increasing strength and performance characteristics. This unit is known to be faster and stronger than units twice its weight.

For ease of fabrication and maintenance, the elbow may be provided a quick disconnect method of attachment that provides 270 degrees of support.

The preferred materials are:
1. Fiberglass reinforced (0 to 40%) (40% preferred) polycarbonate or acetal plastic, urethane, or nylon for moldings.
2. A flexspline of acetal resin, or a fiber glass filled resin such as polyester or nylon, or alternatively, if greater strength is needed, at additional cost, steel can be used for the flexspline and, possibly, for the rigid spline teeth. Graphite fibers may also be used for filling material, especially with nylon.

Polycarbonate has the best properties for the purpose, good dimensional stability in molding, does not absorb moisture, and does not warp. Acetal resin has similar properties and a low coeffecient of friction as well as being thermoplastic in contrast to epoxy resin which is thermosetting. Graphite fibers are very light weight and help strengthen the moldings and lubricate what they contact.

The working of this invention may become clearer from a study of the accompanying figures.

Figure 1:
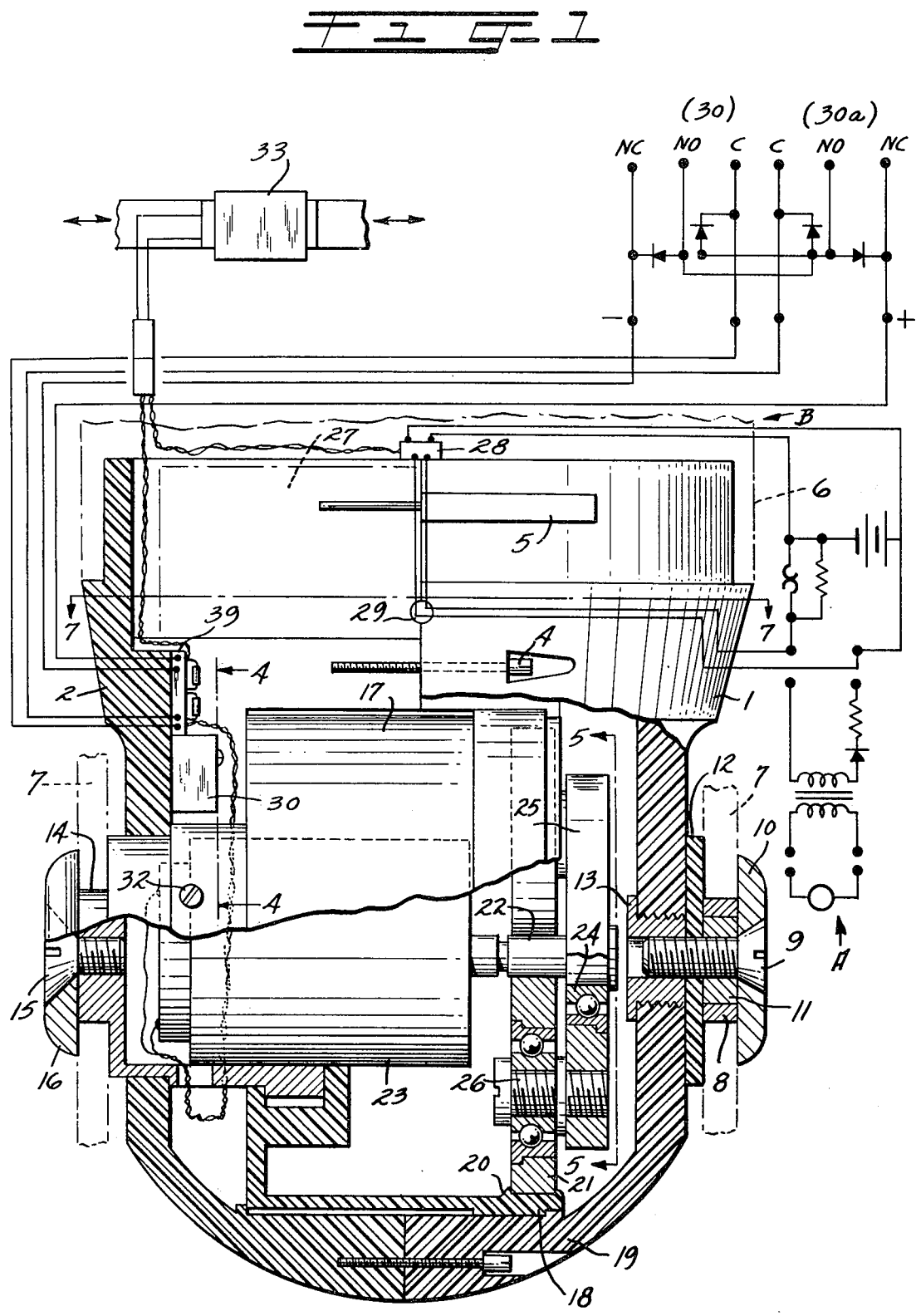
FIG. 1 is a cut away view of the joint prosthesis in a basic configuration with the battery inserted, and the elbow actuator connected, and the circuitry for the limit switch assembly and the thermal cut-out schematically diagrammed.

In FIG. 1, the passive housing 1, so called because the output for moving the forearm does not come through that side, matches the active housing 2 and is secured to the passive housing 1 by screws and threaded inserts 4. The upper part of the elbow is formed into a quick disconnect joint 5 to mate with the humeral unit 6 although another connection is used where the individual uses a conventional humeral turntable prosthesis. The quick disconnect has the advantage of simpler construction and the ability to include the battery and chager making the joint a self contained, powered unit. The forearm 7 is pivoted on the passive housing on a hard anodized bearing race 8 held in place by a screw 9, tightened on a beveled washer 10 securely holding a sintered oilite bearing 11 against a nylon washer 12 and supported in the housing by a knurled threaded insert 13. Coming out of the active housing section 2 is a square output tang 14 which drives the forearm 7 and retains the forearm 7 by means of a left handed screw 15 and beveled washer 16. A flexspline 17 is flexible and has teeth on its external surface 18 that mesh with the rigid teeth of the housing 19. The number of teeth on the flexspline 18 is less than that on the rigid spline 19 so that normally the two splines could not mesh. However, inside the flexspline may be a race 20 and roller bearings, usually two 21 which press against a shaft 22 of a motor 23 which is attached to the flexspline 17. This is believed to be the first use of a raceway in a planetary wave generator of the 2 lobed type. The diameter of the roller bearing 21 and the sun shaft 22 is greater than the diameter of the released flexspline 17; however, when the roller bearings and shaft are inserted into the eliptically distorted flexspline 17, the greater diameter of the flexspline 17 matches the inner diameter of the housing 19 and the flexspline 17 meshes with the rigid spline 19 at the points where the roller bearings 21 contact the flexspline 17. At the same time, the race 20 distributes the pressures of the bearings 21 over a larger surface of the flexspline 17 contributing to the strength of this device. A roller bearing 24 mounted on the shaft 22 may connect the shaft 22 to a wave generator body 25, which we shall describe further in several forms. The function of the wave generator body 25, if used, is to constrain the planetary rollers 21, when only two are used, to act at 180° from each other for which purpose said planetary rollers 21 are each attached to said generator body by a screw 26, although the forces acting on the rollers tend to keep the rollers opposite each other, naturally.

The function of the channel in the wave generator body is to minimize the weight of the unit and it may improve the wear and resiliency of the wave generator and maximize the life of the wave generator by keeping the moving parts in maximal contact through out the life of the unit.

If the length of the user's humeral stump permits, a battery 27 can be mounted in the quick disconnect part of the elbow along with a battery charging shut-off thermostat with thermal hold heating element in parallel and in thermal contact with the shut off 28 and a battery charger connector socket mounted in the housing 29 to permit rapid charging of the battery pack 27 and the maintenance of the charge by maintaining a constant, non-destructive, trickle charge after the batteries have been fully charged. Diagram A of FIG. 1 illustrates this circuitry. Previous electric elbows, such as the Gilmatic Electric Elbow, mounted their battery and charger on the waist of the user. The use of a thermal hold relay 28 is new in elbow prostheses.

Adjacent to the output tang and inside the housing 2 is a set of microswitches 30 and a limit assembly 31 which can stop the forearm 7 from rotation in the direction of rotation when activated by a limit actuating screw 32 mounted on the interior portion of the output tang 14. In between the limits of rotation set by the microswitches 30 and the actuating screws 32 the movement of the elbow is controlled by an external device, a pull switch device 33 or an electromyograph (EMG) device being two known methods of operation.

The limits of rotation circuitry can best be illustrated by the circuit Diagram B of FIG. 1, where it can be seen that current normally flows in either direction through the normally closed (NC) and common (C) contacts and if either of the microswitches are tripped, then the current can only flow in the reversed direction. For example, if the microswitch near the positive pole of the battery were tripped 30a, the normally closed contact (NC) would be opened but, because of the diode connecting the normally closed (NC) and normally open (NO) contacts, current could not be sent to the motor from the battery while, if the battery were reversed, current could flow in the reverse direction through the normally open contact (NO), which is temporarily closed, or the motor can be used as a generator, but the "generator" would be generating into a closed circuit if it were to try to operate in the "forward" direction. The same considerations apply to the other microswitch 30.

While limit switches are known to the art, the simplicity of construction and effeciency of my switch help meet the basic requirement for electric elbows minimum weight and maximum effeciency in movement and resistance to unwanted movement.

In heavy duty applications, an overload release may be mounted between the bell end of the flexspline and the output tang. An "overload release" is a device designed to allow a machine to yield to loads that would destroy the machine if the machine could not be designed to lose its rigid, driving, configuration under such conditions.

Figure 2:
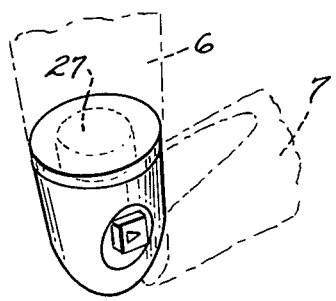
FIG. 2 shows the relationship of the elbow to the forearm and humeral units.

FIG. 2 shows the interrelationship of the different portions of the prosthetic device. The humeral section 6 with quick disconnect attachment means is molded on the intact elbow, 1 and 2 and provides room, in general, for the mounting of the battery pack 27 within the elbow. The forearm unit 7 is seen attached to the elbow 1 and 2.

Figure 3:
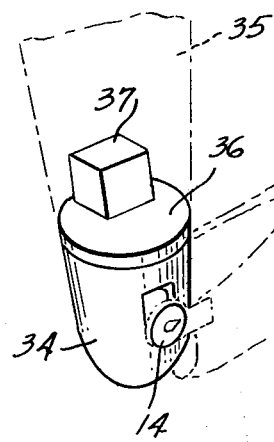
FIG. 3 shows the conventional humeral section modified to accept the humeral section battery pack and the elbow in the configuration to fit the conventional humeral elbow turntable.

FIG. 3 shows a modified elbow 34 for matching with a standard humeral prosthesis 35 by providing a baseplate 36 that will properly mate with the elbow turntable of the humeral prosthesis 35. In such situations, the battery pack may be arranged differently 37 and be mounted inside the humeral element 35 of the prosthesis. On the output tang 14 may be provided a marking ("A" in the present case) for determining the orientation of forearm 7 to the elbow 34.

Figure 4:
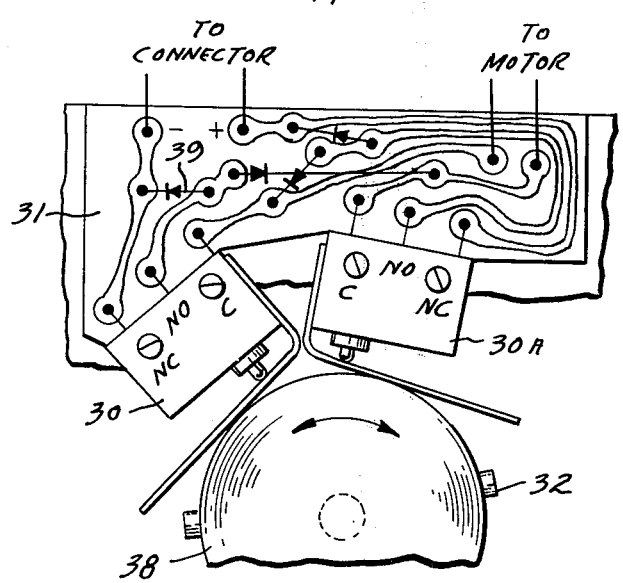
FIG. 4 shows details of the limit switch assembly and electric circuitry.

FIG. 4, taken along the line 4—4 of FIG. 1, shows details of the forearm rotation limit assembly. The microswitches 30 and 30a with their normally closed (NC), normally open (NO) and common (C) contacts which are controlled by the limit actuating screws (32) mounted on the interior portion 38 of the output tang. The printed circuit board 31 is connected to the battery 27 or 37 and to the motor 23 and is used to switch the modes of operation of the elbow in conjunction with the diodes 39.

Figure 5:
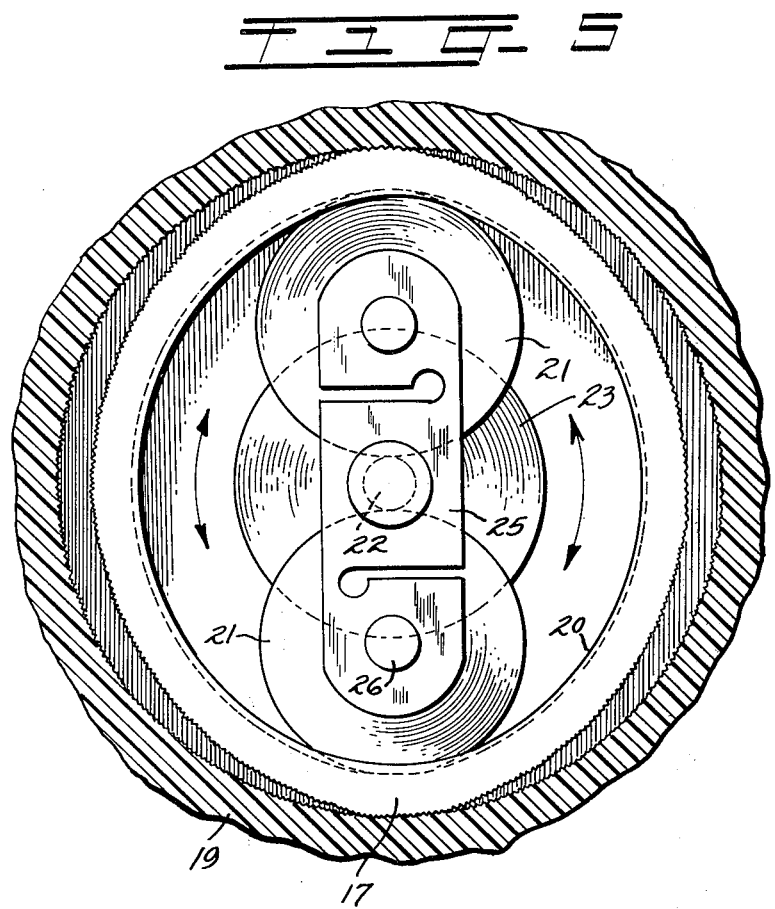
FIG. 5 shows the planetary roller wave generator with my modified wave generator body instead of the conventional body.

FIG. 5, taken along the line 5—5 of FIG. 1, shows a face on view of the planetary wave generating assembly. The unequal size of the flexspline 17 and the rigid spline housing 19 are apparent. The wave generator body 25 is an improved resilient, balanced forces wave generator body. The value of the improved generator body is the ability of the body 25 to maintain good alignment and pressures over a wide variation of roller diameters and therefore assure proper performance over a long operating life. The race 20 can also be seen as a constraint on the movement of the planetary rollers 21 and a means of distributing the contace area between the planets 21 and the flexspline 17.

Figure 6:
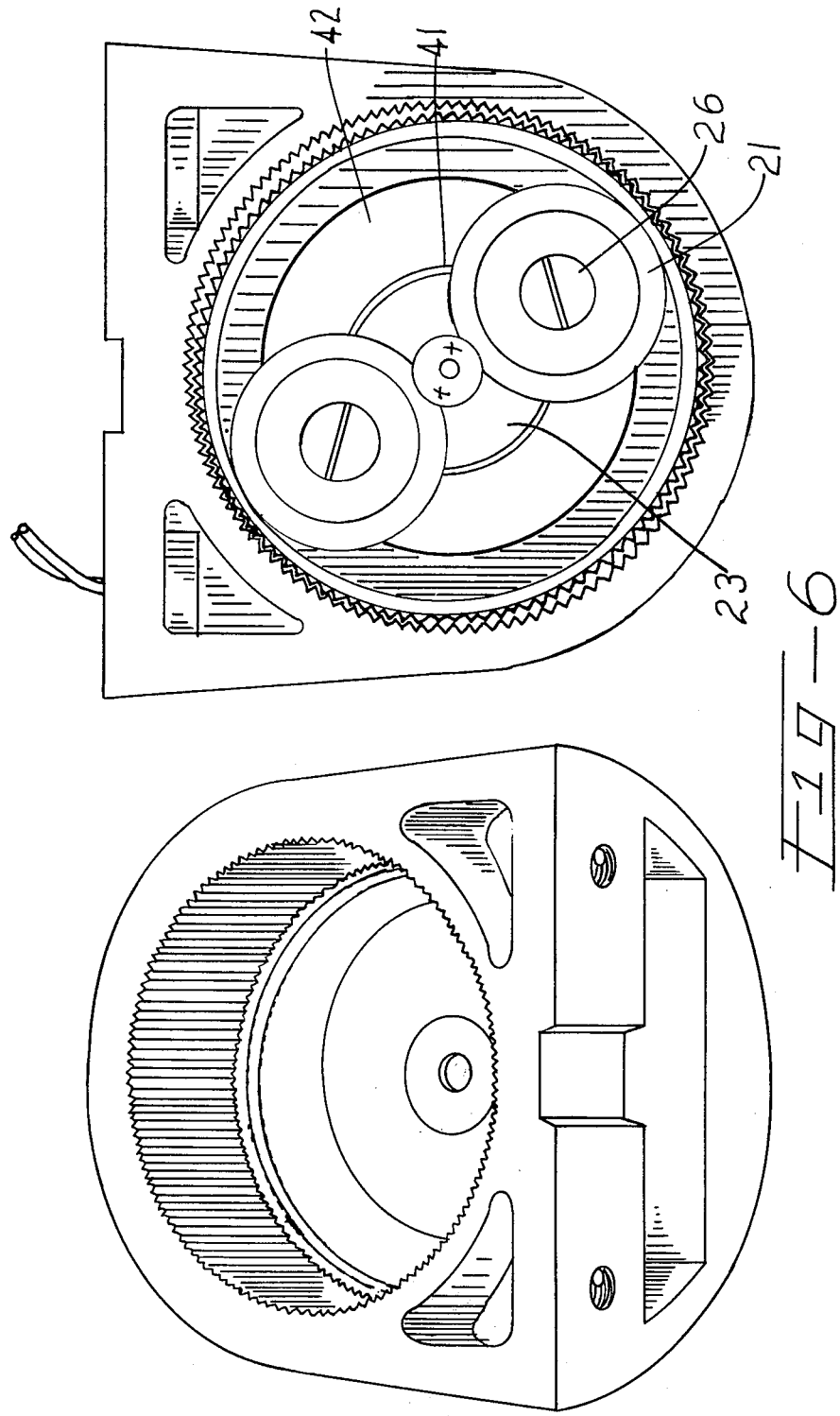
FIG. 6 shows the details of a roller bearing wave generator body and the presence of a bi-directional no back which is especially valuable in heavy duty uses.

FIG. 6, taken in the same plane as FIG. 5, shows another improved version of the wave generator body where the wave generator is supported by the motor housing, reducing the bearing speed by a factor of the planetary reduction ratio. Around the motor 23 is mounted a ball bearing 41 and on the ball bearing 41 is mounted a collar 42 through which are mounted the planetary rollers 21 by the screws 26. The advantage of this method is that the high speed bearing 24 has been replaced by a low speed bearing 41 giving longer wear and requiring less power. In addition, between the motor 23 and the sun shaft may be inserted a bi-directional no back, a drive driven lock, which permits power to be transmitted from motor 23 to shaft 22 to planets 21 to drive the planets in either direction but locks the shaft or sun 22 against the housing if it attempts to backdrive. The use of the no back can increase the efficiency of the system to approximately 95%.

A bi-directional no back drive driven lock is a lock that is driven by a motor and is designed to insure that the member being driven can not be driven in the direction opposite to the driving direction. "Bi-directional" refers to the ability of the device to operate with motors that can drive in both forward and reverse directions. "No back drive" refers to the ability to move the member in only the direction intended and not backward. "Driven lock" refers to the fact that this device is a passive tool to prevent motors from experiencing forces that would move the device in the backwards direction.

No backs ae discussed in the *Formsprag* catalog available from General Chain and Belt Company, 292 Lafayette St., New York 10012, N.Y.

Figure 7:
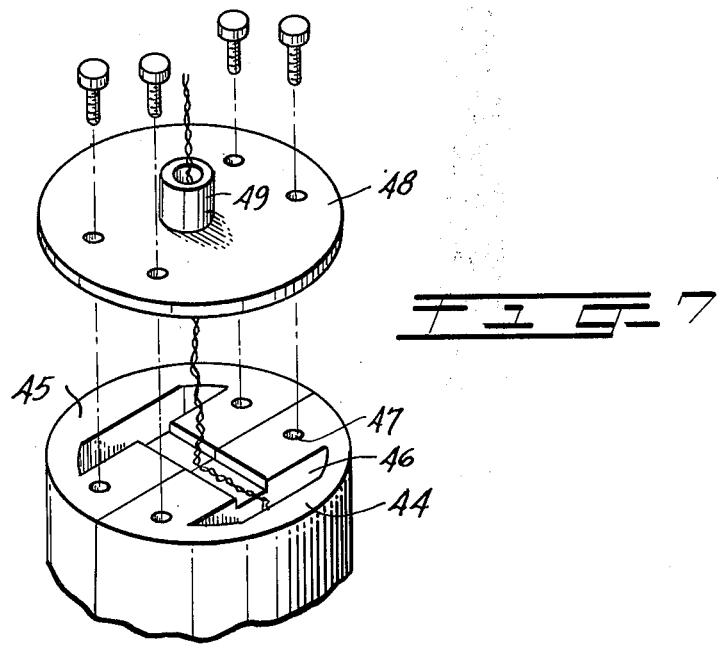
FIG. 7 shows the modified housing indicating the baseplate for use in conjunction with a conventional humeral unit.

FIG. 7 is taken in plane 7—7 of FIG. 1. It is a view of a modification of the elbow housing to permit the use of the elbow with a conventional humeral turntable prosthetic device. The housings 44 and 45 have been modified by removing the quick disconnect configuration at approximately the 7—7 plane and now the limit assembly slot 46, where the limit assembly consisting of the microswitches 30 and electronic circuitry 31 are inserted, is visible. Screw holes 47 and a baseplate 48 holds the two housing sections 44 and 45 together. The screw for attaching the elbow to the conventional humeral section 35 is hollow allowing control wires and battery connections to pass between the elbow and the humeral section.

Figure 8:
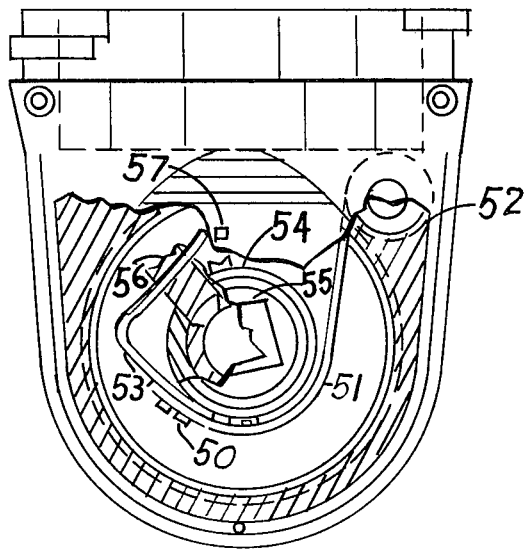
FIG. 8 is a sectional view of an elbow showing the counterbalancing and overload release construction.

In FIG. 8:

Counterbalancing is accomplished by fastening at 50 a constant force spring 51 to the elbow output 14 to apply a torque counter to that caused by the weight of the forearm 7 and hand. The other end of the spring 51 reacts against a storage bushing 52 in the elbow housing 2.

Overload release and full extension release is accomplished by fabricating the elbow output 14 in two pieces, the flexspline output 54 and the released output tang 55. The released output tang 55 can rotate within the flexspline 54 when the locking pin 56 is moved outward. The locking pin 56 is held in place by a preloaded retaining spring 53 which applies a force pushing the locking pin 56 thru the flexspline output 54 into the output tang 55. This retaining spring 53 is attached and reacts against the flexspline output 54.

When the output 55 torque exceeds the desired limit, the locking pin 56 is driven out by the radial force component between the tapered nose of the locking pin 56 and the output tang 55 overcoming the retaining spring 53. The forearm 7 is now free to rotate, until the pin 56 again lines up with the recess in the output 55, at which time it will reset. This release may also be activated by the full extension limit pin 57 in the housing 2 pushing the spring 53 outward as the flexspline output 54 rotates to full extension. This resets when the flexspline output 53 rotates off the limit 57 and the pieces again line up.

Figure 9A:
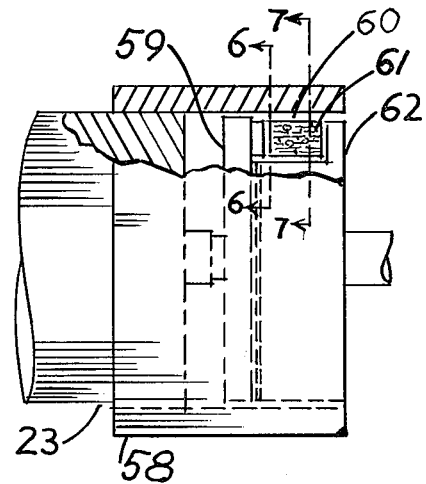
FIGS. 9a, 9b and 9c are views for part of an elbow showing the construction of a no-back.

In FIG. 9a:

The effeciency of the elbow system may be increased if an automatic locking device such as a reverse-locking clutch (no back) or a spring applied brake is incorporated between the motor 23 and the flexspline 17. A reverse-locking clutch permits the motor 23 drive shaft to drive the sun roller 22, but if the sun roller were to back drive the motor 23, the torque would be transmitted to the reverse-locking clutch housing 58 and resisted. This is accomplished by; attaching the motor 23 output shaft to the reverse-locking clutch input key 59. On this key are multiple shouldered pins that support the locking rollers 60 with the support springs 61. These rollers 60 wedge between the reverse-locking clutch output cam 62 and the housing 58, when a torque greater than that available from the motor 23 is applied to the output 62. When the torque available from the motor is greater than the load, the force is transmitted from the motor 23 thru the shoulders on the pins of the key 59 to the output 62 and to the attached sun roller 22. The springs 61 within the rollers 60 permit the rollers 60 to float freely when they are being pushed out of the wedge by contact of the housing 58 on them in the unlocked condition and permit them to lock in the wedge between the housing 58 and the output 62 when in the locked condition.

Figure 9B:
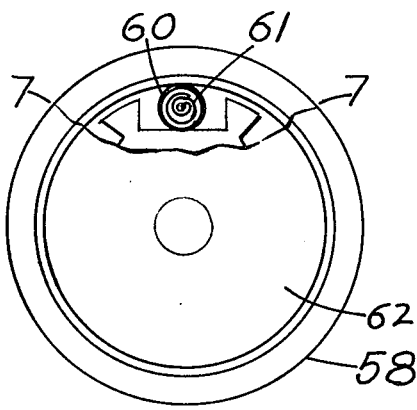

In FIG. 9b, taken as a section along the plane b—b of FIG. 9a, looking in the direction of the arrows b—b, the locking rollers 60 and support springs 61 can be seen.

Figure 9C:
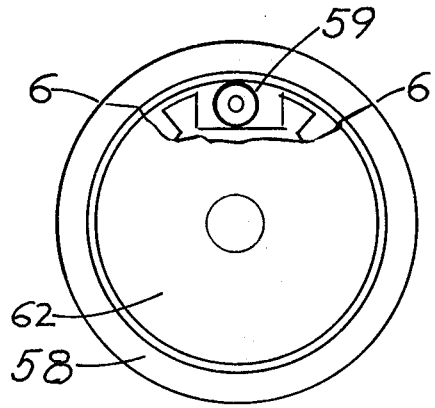

In FIG. 9c, taken as a section along the plane c—c of FIG. 9a, looking in the direction of the arrows c—c, the clutch input key 59 can be seen.

Figure 10:
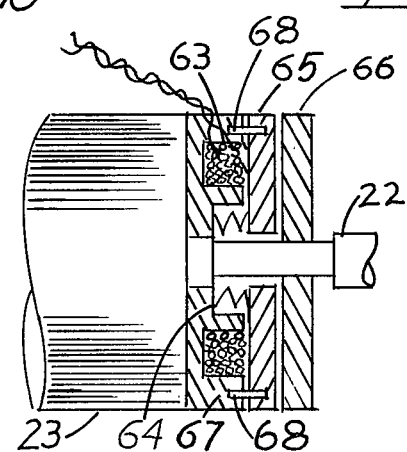
FIG. 10 illustrates an electric spring brake which releases when power is supplied and can be used with a torque servo motor.

In FIG. 10:

The spring applied brake is incorporated on the motor 23 output shaft. The electro-magnet coil 63 and the soft iron housing 67 are attached to the motor housing. The coil 63 leads are connected to the motor power source 30 and receives power when the motor does. When power is supplied, the coil 63 pulls the fixed friction brake surface 65 away from the rotating friction surface 66, attached to the motor 23, compressing the brake springs. This lets the motor shaft rotate freely. When power is removed, the spring 64 pushes the fixed friction brake surface 65 against the rotating friction surface 66. The torque from the sun shaft 22 is now transmitted thru the rotating friction surface 66 to the fixed brake surface 65 thru the fixed pins 68 to the housing 67 to the motor 23 housing. If more torque is applied to the friction surfaces than they can support, they will slide releasing the overload.

In its preferred embodiment, my invention has characteristics that can surpass any of the existing devices in their functional characteristics. Some achievable characteristics of my invention are:

| | |
|---|---|
| Weight of elbow (without battery) | 11 oz. (standard) |
| | 14 oz. (heavy duty unit using steel flexspline) |
| Weight of battery pack: | 10 oz. (conventional upper arm mounting) |
| | 8½ oz. (elbow mounting) |
| SPEED: | less than two seconds for an 18 inch pound load. |
| POWER: | sufficient to operate the unit 18 hours and 1200 loaded cycles without discharging the batteries beyond 1.1 Volts per cell (Nickel-Cadmium). |
| NOISE: | less than 60 db measured at 1 meter on the C scale. |
| SIZE: | width across axis is 2¼ in. axis of rotation to stump end: (without battery and in quick disconnect configuration) 1½ in. (with battery) 3 in. (conventional configuration without battery (which goes into humeral section)) 2 in. |
| RANGE OF MOTION: | 10 degrees to 135 degrees, nominal can be increased to: 0 degrees to 145 degrees, nominal |

Parts of this invention have been disclosed in *Bulletin of Prosthetics Research*, numbers 10—10 through 10–12, Fall 1968 to Fall 1969. This application seeks protection for the improved electric elbow to the extent that it has not been disclosed by the aforementioned disclosures. Furthermore, the U.S. Government retains certain rights in this invention as explained in USC 38 Section 652 (a) Executive Order 10096, subparagraph (b).

While I have described my invention in its preferred embodiment, it is understood that modifications can be made therein by those skilled in the art without departing from the spirit of the invention whose scope is defined by the following claims.

I claim:

1. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell end coaxial with the axis of revolution of the flexible member (flexspline), and a limit assembly within the housing comprising two microswitches and four Diodes, whereby the motor may be shunted and power shut off at the limits wherein the improvement comprises:
a raceway inserted between the planetary rollers and the flexspline whereby the torque load within the flexspline is distributed and the load concentration under the planetary rollers is decreased.

2. An improved prosthetic joint, as in claim 1, wherein the permanent magnet electric motor comprises a bell wound servo motor.

3. An improved prosthetic joint, as in claim 1, wherein the permanent magnet electric motor comprises a torque servo motor.

4. An improved prosthetic joint, as in claim 1, wherein the planetary roller reduction harmonic drive wave generator further comprises a smooth surface shaft or sunroller in intimate contact with the planetary rollers constrained by a wave generator body whereby the forces between the sun and planets generated by the harmonic drive are balanced.

5. An improved prosthetic joint, as in claim 4, wherein the wave generator body comprises:
a. mounted on the body of the motor at the output and, a bearing;
b. mounted on the bearing a collar; and
c. means for mounting the planetary rollers on the collar and in intimate contact with the shaft.

6. An improved prosthetic joint, as in claim 4, further comprising a bi-directional no back drive driven lock mounted between the motor output and the shaft or sun roller whereby the motor can drive the sun in either direction but the sun should lock against the housing if it is used to drive the motor.

7. An improved prosthetic joint device as in claim 6, wherein an electric spring brake is mounted on the motor output shaft.

8. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell end coaxial the axis of revolution of the flexible member (flexspline), and a limit assembly within the housing comprising two microswitches and four Diodes, whereby the motor may be shunted and power shut off at the limits wherein the improvement comprises:
- a raceway molded into the flexspline whereby the load concentration under the planetary rollers is decreased and the torque load is distributed by the flexspline.

9. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell end coaxial with the axis of revolution of the flexible member (flexspline), and a limit assembly within the housing comprising two microswitches and four Diodes, whereby the motor may be shunted and power shut off at the limits wherein the improvement comprises:
- an overload release mounted between the bell end of the flexspline and the output tang.

10. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell and coaxial with the axis of revolution of the flexible member (flexspline), and a limit assembly within the housing comprising two microswitches and four Diodes, whereby the motor may be shunted and power off at the limits wherein the improvement comprises:
- a. in part a quick disconnect section wherein is placed a battery pack;
- b. a thermal cut out switch is mounted on the battery pack;
- c. a resistor is attached in parallel with and in intimate contact with the thermal cut out causing it to act as a thermal holding relay; and
- d. the thermal cut out is connected to a battery charger socket in the improved prosthetic joint housing, whereby the battery may be rapidly charged and when fully charged can be maintained by a continuous trickle charge.

11. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell and coaxial with the axis of revolution of the flexible member (flexspline), and a limit assembly within the housing comprising two microswitches and four Diodes, whereby the motor may be shunted and power shut off at the limits wherein the improvement comprises:
- a. attached to the output tang, externally to the joint a driven artificial limb such as a forearm;
- b. opposite to the output tang on the surface of the joint, a means of pivotally attaching said driven artificial limb, and
- c. a means to counterbalance the weight of the driven artificial limb mounted in the means for pivotally attaching said driven artificial limb.

12. An improved prosthetic joint, as in claim 11, wherein the counterbalancing means is spring loaded.

13. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell and coaxial with the axis of revolution of the flexible member (flexspline), and a limit assembly within the housing comprising two microswitches and four Diodes, whereby the motor may be shunted and power shut off at the limits wherein the limit assembly further comprises:
- a. a lead from a battery to the first microswitch at a normally closed contact;
- b. a lead from a common contact of the first microswitch to the motor;
- c. a lead from the motor to a common contact of the second microswitch;
- d. a lead from a normally closed contact of the second microswitch to another terminal of the battery;
- e. a lead connecting a normally opened contact of the first microswitch to a normally opened contact of the second microswitch;
- f. a diode connecting the lead connecting the normally open contacts to each other to the leads connecting the normally closed contacts and the battery; and
- g. a diode connecting the lead connecting the normally open contacts to each other to each of the leads connecting the common contacts and the motor.

14. An improved prosthetic joint device comprising:
- a. a two piece housing of 40% fiberglass reinforced polycarbonate forming an internal rigid spline;
- b. a flexspline meshed within said housing with said rigid spline;
- c. two planetary roller bearings in contact with the interior of said flexspline;
- d. a shaft between said rollers and in intimate contact with each roller;
- e. a servo motor attached to said shaft whereby said shaft is driven;
- f. a bearing around said motor body at the shaft end;
- g. a collar around and on the shaft face of said bearing;
- h. screws for mounting said planetary rollers screwed into said collar whereby to constrain the planets to be at 180 degrees from each other and in intimate contact with said shaft;
- i. an output tang mounted axially on and perpendicular to the teeth of the flexspline;
- j. limit actuating screws mounted on the interior of said output tang;
- k. a limit actuating assembly comprising two microswitches and associated electronic circuitry mounted in said housing whereby said limit actuating screw may operate said microswitch;

l. a thermal cut out and thermal resistor in parallel therewith mounted on a battery whereby said battery may be recharged and maintained on a trickle charge when fully charged, said battery connected to said limit activating switches;

m. a charger receptical electrically connected to said thermal cut out whereby said battery may be charged; and n. a pivotal mounting on the housing opposite said output tang for pivoting a driven artificial extremity such as a forearm.

15. An improved prosthetic joint device as in claim 14, wherein the servo motor is a torque servo motor, wherein the flexspline is made of steel, wherein a bidirectional no back drive driven lock is inserted between the torque servo motor and the shaft and an overload release is mounted between the bell end of the flexspline and the output tang.

16. An improved prosthetic joint device as in claim 15, wherein a baseplate is mounted joining the two housings and a hollow screw is provided in the baseplate connecting the joint to the conventional type humeral turntable prosthesis, and the battery thermal cutout and the charging socket are mounted in said conventional type humeral prosthesis.

17. An improved prosthetic joint device, as in claim 15, wherein the housing forms an integrally molded quick disconnect, wherein the battery is mounted in the quick disconnect section of the housing a and wherein said charging socket is mounted in the housing of said prosthetic joint.

18. An improved prosthetic joint device as in claim 14, wherein said flexspline is of acetal resin, wherein a steel raceway is inserted in said flexspline between said flexspline and said planetary rollers, wherein the servo motor is bell wound and wherein a counterbalance is mounted in said pivotal mounting, whereby a terminal device may be counterbalanced.

19. An improved prosthetic joint device, as in claim 18, wherein a baseplate is mounted joining the two housings and a hollow screw is provided in the baseplate connecting the joint to the conventional type humeral turntable prosthesis, and the battery and thermal cut out and the charging socket are mounted in said conventional type humeral prosthesis.

20. An improved prosthetic joint device, as in claim 18, wherein the housing forms an integrally molded quick disconnect, wherein the battery is mounted in the quick disconnect section of the housing and wherein said charging socket is mounted in the housing of said prosthetic joint.

21. An improved prosthetic joint comprising: a housing forming an internal rigid circular spline internally meshing with a flexible member, forming externally a spline and internally a circular cavity, said cavity containing a permanent magnet electric motor driving a planetary roller reduction harmonic drive wave generator, said flexible member, comprising an open cylindrical section closed on one end by a planar section (the bell end) forming a rigid output tang on the bell end coaxial with the axis of revolution of the flexible member (flexspline), and a limit assembly within the housing comprising two microswitches and four Diodes, whereby the motor may be shunted and power shut off at the limits, wherein the planetary roller reduction harmonic drive wave generator further comprises a smooth surface shaft or sunroller in intimate contact with the planetary rollers constrained by a wave generator body whereby the forces between the sun and planets generated by the harmonic drive are balanced, wherein the wave generator body is further improved, comprising the formation within the wave generator body of a channel between the attachment of the shaft and the attachment of each planetary roller, said channel being perpendicular to the line between the attachments of the planets and shaft and sufficiently long to make the planets movable (preloaded) relative to the shaft whereby the planets and shaft can be kept in intimate contact throughout an extended lifetime.

* * * * *